United States Patent [19]
Keil et al.

[11] Patent Number: 4,948,415
[45] Date of Patent: Aug. 14, 1990

[54] AGENTS FOR REGULATING PLANT GROWTH

[75] Inventors: Michael Keil, Freinsheim; Dieter Jahn, Edingen-Neckarhausen; Dieter Kolassa, Ludwigshafen; Ulrich Schirmer, Heidelberg; Rainer Becker, Bad Durkheim; Johann Jung; Wilhelm Rademacher, both of Limburgerhof, all of Fed. Rep. of Germany

[73] Assignee: BASF Aktiengesellschaft, Ludwigshafen, Fed. Rep. of Germany

[21] Appl. No.: 305,611

[22] Filed: Feb. 2, 1989

Related U.S. Application Data

[62] Division of Ser. No. 876,759, Jun. 20, 1986, abandoned.

[30] Foreign Application Priority Data

Jun. 21, 1985 [DE] Fed. Rep. of Germany ....... 3522213

[51] Int. Cl.$^5$ ............... A01N 43/78; A01N 43/02; C07D 277/24; C07D 263/34
[52] U.S. Cl. ............................ 71/90; 71/76; 71/78; 548/182; 548/183; 548/187; 548/204
[58] Field of Search .............. 71/90, 76, 78, 88; 548/204, 187, 182, 183

[56] References Cited

U.S. PATENT DOCUMENTS

| | | | |
|---|---|---|---|
| 3,950,420 | 4/1976 | Sawaki et al. | 71/90 |
| 4,584,013 | 4/1986 | Brunner | 71/88 |
| 4,602,935 | 7/1986 | Becker et al. | 71/88 |
| 4,604,132 | 8/1986 | Conway et al. | 71/90 |
| 4,650,513 | 3/1987 | Becker et al. | 71/88 |
| 4,842,638 | 6/1989 | Kast et al. | 71/90 |

FOREIGN PATENT DOCUMENTS 0163362 9/1984 Japan ........................ 71/88

Primary Examiner—Richard L. Raymond
Assistant Examiner—Raymond Covington
Attorney, Agent, or Firm—Keil & Weinkauf

[57] ABSTRACT

Agents for regulating plant growth containing an effective amount of at least one cyclohexenone derivative of the formula

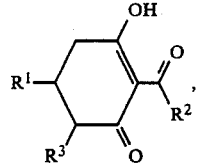

where $R^1$, $R^2$ and $R^3$ have the meanings given in the disclosure, or a salt thereof, and a process from regulating plant growth.

6 Claims, No Drawings

AGENTS FOR REGULATING PLANT GROWTH

This is a division of application Ser. No. 876,759, filed Jun. 20, 1986 now adandoned.

The present invention relates to agents based on cyclohexenone derivatives which regulate the growth of plants, and to a process for regulating plant growth.

Certain 2-acyl-3-hydroxycyclohex-2-en-1-ones which regulate plant growth have been described (EP-A-123,001 and EP-A-126,713).

We have now found novel agents for regulating plant growth which are characterized by an effective amount of at least one cyclohexenone derivative of the formula

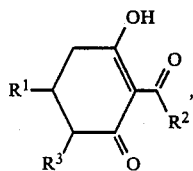
(I)

where $R^1$ is a 5- to 7-membered heterocycle having 1 to 3 identical or different hetero-atoms or ring members selected from the group consisting of N, O, S, SO or $SO_2$ and which may contain up to 3 substituents from the group consisting of alkyl, alkenyl, alkoxy, alkoxyalkyl or alkylthio, each of 1 to 6 carbon atoms, cyclohexyl, cyclohexoxy, phenyl which is unsubstituted or substituted by methyl, chloro or methoxy, phenoxy which is unsubstituted or substituted by methyl, chloro or cmethoxy, halogen, nitro or dialkylamino, $R^2$ is alkyl of 1 to 4 carbon atoms, alkoxyalkyl of 1 to 4 carbon atoms, cyclopropyl, benzyl, phenylethyl or acyloxyalkyl of up to 6 carbon atoms, and $R^3$ is hydrogen, alkoxycarbonyl of 2 to 5 carbon atoms or cyano, or a salt thereof.

In formula I, $R^1$ is for example tetrahydropyran-2-yl, tetrahydropyran-3-yl, 6-methoxytetrahydropyran-2-yl, 6-methoxytetrahydropyran-3-yl, tetrahydropyran-4-yl, 4-methyltetrahydropyran-3-yl, 3-methyltetrahydropyran-4-yl, tetrahydrothiopyran-2-yl, tetrahydrothiopyran-3-yl, $\Delta^3$-dihydrothipyran-3-yl, tetrahydrofuran-3-yl, 1-oxotetrahydrothiopyran-3-yl, 1,1-dioxotetrahydrothiopyran-3-yl, tetrahydrothein-3-yl, 2,2-dimethyltetrahydrothien-3-yl, pyrid-2-yl, pyrid-3-yl, 2-isopropyl-1,3-dioxepan-5-yl, tetrahydrofuran-2-yl, 1,1-dioxo-2,2-dimethyltetrahydrothien-3-yl, fur-2-yl, 2-methylfur-5-yl, fur-3-yl, 2-thienyl, 3-thienyl, 1-methylpyrrol-2-yl, 1-methyl-pyrazol-4-yl, 3-phenyl-isoxazol-5-yl, 4-methylisothiazol-5-yl, 2-methylthiazol-5-yl, 2-dimethylaminothiazol-5-yl, 5,5-dimethyl-1,3-dioxan-2-yl, isothiazol-5-yl, 4-methylisothiazol-5-yl, 2-methoxypyridin-5-yl, 2,6-dimethoxypyridin-3-yl and 2-methylpyridin-6-yl.

$R^2$ is for example methyl, ethyl, n-propyl, isopropyl, n-butyl, sec-butyl, isobutyl, tert-butyl, cyclopropyl, benzyl, phenylethyl, methoxyethyl, acetoxymethyl and propionoxyethyl, and $R^3$ is for instance hydrogen, methoxycarbonyl, ethoxycarbonyl and cyano.

Suitable salts of compounds of the formula I are agriculturally useful salts, such as alkali metal salts, especially potassium and sodium salts, alkaline earth metal salts, especially calcium, magnesium and barium salts, manganese, copper, zinc and iron salts, and ammonium, phosphonium, sulfonium and sulfoxonium salts, e.g., tetraalkylammonium salts, benzyltrialkylammonium salts, trialkylsulfonium salts and trialkylsulfoxonium salts.

It is known from DE-A-2,439,104, DE-A-3,121,355, DE-A-3,123,312, DE-A-3,324,707, DE-A-3,340,265, DE-A-3,303,182, DE-A-3,342,630, EP-A-102,823, EP-A-104-876, EP-A-125,094 and the older German applications P 34 20 229.8, P 34 29 437.6 and P 34 37 238.5 that the cyclohexenone derivatives of the formula I are used as intermediates for the synthesis of herbicides.

The various synthesis variants for the cyclohexenone derivatives are given in the above literature. The synthesis of 2-butyryl-3-hydroxy-5(3-isopropylisoxazol-5-yl)cyclohex-2-en-1-one is described below by way of example.

MANUFACTURING EXAMPLE 15.1 g of the sodium salt of 5-(3-isopropylisoxazol-5-yl)-4-methoxycarbonylcyclohexane-1,3-dione was suspended in 150 ml of tetrahydrofuran; 6.4 g butyryl chloride was added while cooling with ice. After the mixture had been stirred for 15 hours it was filtered and concentrated. The residue obtained was taken up in methylene chloride, 2 g of 4-(N,N-dimethylamino)-pyridine was added, and the mixture was stirred for 3 days. After shaking with 10 wt % hydrochloric acid and then with water, the mixture was dried over sodium sulfate and concentrated. 15 g of 2-butyryl-3-hydroxy-5(3-isopropylisoxazol-5-yl)-4-methoxycarbonylcyclohex-2-en-1-one was obtained as an isomer mixture, and was then stirred with 300 ml of 10 wt % strength sodium hydroxide solution at 25° C. for 16 hours. The pH of the solution was then adjusted to 2 concentrated hydrochloride acid, and stirring was carried out for 2 hours at 85° C. After cooling the product was filtered off, washed with water and recrystallized from isopropanol. There was obtained 2-butyryl-3-hydroxy-5(3-isopropylisoxazol-5-yl)-cyclohex-2-en-1-one of m.p. 105°-107° C. (compound no. 64).

In the following Table 1, physical data (NMR spectra) are given for various compounds; these compounds have been prepared and examined as to biological action. The remaining compounds can be prepared analogously, and they are expected, in view of their structural similarity, to have a similar biological action.

TABLE 1

$(R^3 = H)$

| Compound no. | $R^1$ | $R^2$ | physical data+ |
|---|---|---|---|
| 1 | tetrahydrofuran-2-yl | ethyl | |
| 2 | tetrahydrofuran-2-yl | propyl | |
| 3 | tetrahydrofuran-3-yl | ethyl | |
| 4 | tetrahydrofuran-3-yl | propyl | |
| 5 | 2-methyl-tetrahydrofuran-3-yl | ethyl | |
| 6 | 2-methyl-tetrahydrofuran-3-yl | propyl | 0.98(t); 1.18(d) 3.08(t) |
| 7 | 2,2-dimethyl-tetrahydrofuran-3-yl | ethyl | |
| 8 | 2,2-dimethyl-tetrahydrofuran-3-yl | propyl | |
| 9 | tetrahydrothien-3-yl | ethyl | 1.16(t); 1.5–3.3(m) |
| 10 | tetrahydrothien-3-yl | propyl | 0.99(t); 1.3–3.2(m) |
| 11 | 2,5-dihydrothien-3-yl | ethyl | |
| 12 | 2,5-dihydrothien-3-yl | propyl | |
| 13 | 2,2-dimethyl-2,5-dihydrothien-3-yl | ethyl | |
| 14 | 2,2-dimethyl-2,5-dihydrothien-3-yl | propyl | |
| 15 | 2,2-dimethyl-1-oxo-2,5-dihydrothien-3-yl | ethyl | |
| 16 | 2,2-dimethyl-1-oxo-2,5-dihydrothien-3-yl | propyl | |
| 17 | 2,2-dimethyl-1,1-dioxo-2,5-dihydrothien-3-yl | ethyl | |
| 18 | 2,2-dimethyl-1,1-dioxo-2,5-dihydrothien-3-yl | propyl | |
| 19 | 1-oxo-tetrahydrothien-3-yl | ethyl | |
| 20 | 1-oxo-tetrahydrothien-3-yl | propyl | |
| 21 | 1,1-dioxo-tetrahydrothien-3-yl | ethyl | |
| 22 | 1,1-dioxo-tetrahydrothien-3-yl | propyl | |
| 23 | 1-oxo-2,2-dimethyl-tetrahydrothien-3-yl | ethyl | |
| 24 | 1-oxo-2,2-dimethyl-tetrahydrothien-3-yl | propyl | |
| 25 | 1,1-dioxo-2,2-dimethyl-tetrahydrothien-3-yl | ethyl | |
| 26 | 1,1-dioxo-2,2-dimethyl-tetrahydrothien-3-yl | propyl | |
| 27 | 2-methyl-dihydro-1,3-dithiol-2-yl | ethyl | |
| 28 | 2-methyl-dihydro-1,3-dithiol-2-yl | propyl | |
| 29 | 2-furyl | ethyl | |
| 30 | 2-furyl | propyl | |
| 31 | 2-methyl-5-furyl | ethyl | |
| 32 | 2-methyl-5-furyl | propyl | |
| 33 | 2-chloro-5-furyl | ethyl | |
| 34 | 2-chloro-5-furyl | propyl | |
| 35 | 3-furyl | ethyl | |
| 36 | 3-furyl | propyl | |
| 37 | 2-thienyl | ethyl | |
| 38 | 2-thienyl | propyl | |
| 39 | 3-thienyl | ethyl | |
| 40 | 3-thienyl | propyl | 0.98(t); 3.45(m); 7.00(m); 7.32(m) |
| 41 | 2,5-dimethyl-thien-3-yl | ethyl | |
| 42 | 2,5-dimethyl-thien-3-yl | propyl | 0.98(t); 2.32(s); 2.40(s); 6.55(s) |
| 43 | 2-nitrothien-5-yl | ethyl | |
| 44 | 2-nitrothien-5-yl | propyl | |
| 45 | 1-methyl-pyrrol-2-yl | ethyl | |
| 46 | 1-methyl-pyrrol-2-yl | propyl | 0.96(t); 3.5(s); 5.85(m); 6.25(m); 6.4(m) |
| 47 | 1-phenyl-pyrrol-3-yl | ethyl | |
| 48 | 1-phenyl-pyrrol-3-yl | propyl | 0.95(t); 6.1(m) 6.8(m); 6.9(m); 7.25(s) |
| 49 | 1-methyl-pyrrol-3-yl | ethyl | |
| 50 | 1-methyl-pyrrol-3-yl | propyl | 0.97(t); 3.52(s); 5.84(t, 1H) |
| 51 | 1-isopropyl-pyrrol-3-yl | ethyl | |
| 52 | 1-isopropyl-pyrrol-3-yl | propyl | 0.95(t); 1.4(d); 4.2(m); 6.0(m); 6.55(m); 6.7(m) |
| 53 | 1-(4-tolyl)-pyrrol-3-yl | ethyl | |
| 54 | 1-(4-tolyl)-pyrrol-3-yl | propyl | 0.95(t); 2.35(s); 6.2(m); 6.85(m); 7.0(m); 7.2(s) |
| 55 | 1-methyl-pyrazol-4-yl | ethyl | |
| 56 | 1-methyl-pyrazol-4-yl | propyl | 1.0(t); 3.74(s); 3.9(s); 7.3(s); 7.38(s) |
| 57 | 1-phenyl-pyrazol-4-yl | ethyl | |
| 58 | 1-phenyl-pyrazol-4-yl | propyl | |
| 59 | 3-phenyl-isoxazol-5-yl | ethyl | |
| 60 | 3-phenyl-isoxazol-5-yl | propyl | |
| 61 | 3-methyl-isoxazol-5-yl | ethyl | |
| 62 | 3-methyl-isoxazol-5-yl | propyl | |
| 63 | 3-isopropyl-isoxazol-5-yl | ethyl | 1.06(t); 1.14(d); 5.95(s) |
| 64 | 3-isopropyl-isoxazol-5-yl | propyl | 1.0(t); 1.27(d); 5,95(s) |

TABLE 1-continued

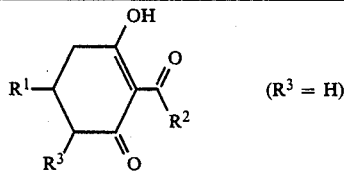

(R³ = H)

| Compound no. | R¹ | R² | physical data+ |
|---|---|---|---|
| 65 | 4-methyl-isothiazol-5-yl | ethyl | |
| 66 | 4-methyl-isothiazol-5-yl | propyl | |
| 67 | 3-methoxymethyl-isoxazol-5-yl | ethyl | |
| 68 | 3-methoxymethyl-isoxazol-5-yl | propyl | |
| 69 | isothiazol-4-yl | ethyl | |
| 70 | isothiazol-4-yl | propyl | |
| 71 | 2-methyl-thiazol-4-yl | ethyl | |
| 72 | 2-methyl-thiazol-4-yl | propyl | |
| 73 | 2-methyl-thizaol-5-yl | ethyl | |
| 74 | 2-methyl-thizaol-5-yl | propyl | |
| 75 | 2-phenyl-thiazol-4-yl | ethyl | |
| 76 | 2-phenyl-thiazol-4-yl | propyl | |
| 77 | 2-(4-chlorophenyl)-thiazol-4-yl | ethyl | |
| 78 | 2-(4-chlorophenyl)-thiazol-4-yl | propyl | |
| 79 | 2-(4-chlorophenyl)-thiazol-5-yl | ethyl | |
| 80 | 2-(4-chlorophenyl)-thiazol-5-yl | propyl | |
| 81 | 2-(4-methoxyphenyl)-thiazol-5-yl | ethyl | |
| 82 | 2-(4-methoxyphenyl)-thiazol-5-yl | propyl | |
| 83 | 2-dimethylamino-thiazol-5-yl | ethyl | |
| 84 | 2-dimethylamino-thiazol-5-yl | propyl | |
| 85 | 1-methyl-5-phenyl-1,2,3-thiazol-4-yl | ethyl | |
| 86 | 1-methyl-5-phenyl-1,2,3-thiazol-4-yl | propyl | |
| 87 | 4-methyl-1,2,3-thiadiazol-5-yl | ethyl | |
| 88 | 4-methyl-1,2,3-thiadiazol-5-yl | propyl | |
| 89 | 3-phenyl-1,2,4-oxadiazol-5-yl | ethyl | |
| 90 | 3-phenyl-1,2,4-oxadiazol-5-yl | propyl | |
| 91 | 2-isopropyl-1,3,4-oxadiazol-5-yl | ethyl | |
| 92 | 2-isopropyl-1,3,4-oxadiazol-5-yl | propyl | |
| 93 | tetrahydropyran-2-yl | ethyl | |
| 94 | tetrahydropyran-2-yl | propyl | |
| 95 | 6-methyl-tetrahydropyran-2-yl | ethyl | |
| 96 | 6-methyl-tetrahydropyran-2-yl | propyl | |
| 97 | 6-methoxy-tetrahydropyran-2-yl | ethyl | |
| 98 | 6-methoxy-tetrahydropyran-2-yl | propyl | |
| 99 | 6-ethoxy-tetrahydropyran-2-yl | ethyl | |
| 100 | 6-ethoxy-tetrahydropyran-2-yl | propyl | |
| 101 | 4-ethyl-6-isobutyloxy-3-methyl-tetrahydropyran-2-yl | ethyl | |
| 102 | 4-ethyl-6-isobutyloxy-3-methyl-tetrahydropyran-2-yl | propyl | |
| 103 | 6-cyclohexyloxy-tetrahydropyran-2-yl | ethyl | |
| 104 | 6-cyclohexyloxy-tetrahydropyran-2-yl | propyl | |
| 105 | 6-benzyloxy-tetrahydropyran-2-yl | ethyl | |
| 106 | 6-benzyloxy-tetrahydropyran-2-yl | propyl | 0.95(t); 3.0(t); 7.3(s) |
| 107 | 6-(4-tolyloxy)-tetrahydropyran-2-yl | ethyl | |
| 108 | 6-(4-tolyloxy)-tetrahydropyran-2-yl | propyl | |
| 109 | 6-benzyloxy-3-methyl-tetrahydropyran-2-yl | ethyl | |
| 110 | 6-benzyloxy-3-methyl-tetrahydropyran-2-yl | propyl | 0.95(t); 3.0(m); 7.3(s) |
| 111 | 6-methoxy-4-phenyl-tetrahydropyran-2-yl | ethyl | |
| 112 | 6-methoxy-4-phenyl-tetrahydropyran-2-yl | propyl | 0.95(t); 3.4(s); 3.5(s); 7.3(m) |
| 113 | tetrahydropyran-3-yl | methyl | |
| 114 | tetrahydropyran-3-yl | ethyl | 60-64 |
| 115 | tetrahydropyran-3-yl | propyl | 0.98(t); 3.02(t); 3.37(t) |
| 116 | tetrahydropyran-3-yl | isopropyl | |
| 117 | tetrahydropyran-3-yl | butyl | |
| 118 | tetrahydropyran-3-yl | isobutyl | |
| 119 | tetrahydropyran-3-yl | benzyl | |
| 120 | tetrahydropyran-3-yl | phenylethyl | |
| 121 | tetrahydropyran-3-yl | methoxyethyl | |
| 122 | tetrahydropyran-3-yl | acetoxymethyl | |
| 123 | tetrahydropyran-3-yl | propionoxyethyl | |
| 124 | 4-methyl-tetrahydropyran-3-yl | ethyl | 0.95(d); 1.1(t); 3.03(q) |
| 125 | 4-methyl-tetrahydropyran-3-yl | propyl | |
| 126 | 4-ethylthio-tetrahydropyran-3-yl | ethyl | |
| 127 | 4-ethylthio-tetrahydropyran-3-yl | propyl | |
| 128 | 2,6-dimethyl-tetrahydropyran-3-yl | ethyl | |
| 129 | 2,6-dimethyl-tetrahydropyran-3-yl | propyl | |
| 130 | 6-methoxy-tetrahydropyran-3-yl | ethyl | |
| 131 | 6-methoxy-tetrahydropyran-3-yl | propyl | |
| 132 | 2,6,6-trimethyl-tetrahydropyran-3-yl | ethyl | |
| 133 | 2,6,6-trimethyl-tetrahydropyran-3-yl | propyl | |
| 134 | 2-methoxy-tetrahydropyran-3-yl | ethyl | |

TABLE 1-continued $(R^3 = H)$

| Compound no. | $R^1$ | $R^2$ | physical data+ |
|---|---|---|---|
| 135 | 2-methoxy-tetrahydropyran-3-yl | propyl | |
| 136 | tetrahydropyran-4-yl | methyl | |
| 137 | tetrahydropyran-4-yl | ethyl | 1.14(t); 3.37(t); 4.02(d) |
| 138 | tetrahydropyran-4-yl | propyl | 0.99(t); 3.02(t); 3.92(m) |
| 139 | tetrahydropyran-4-yl | isopropyl | |
| 140 | tetrahydropyran-4-yl | butyl | |
| 141 | tetrahydropyran-4-yl | isobutyl | |
| 142 | tetrahydropyran-4-yl | benzyl | |
| 143 | tetrahydropyran-4-yl | phenylethyl | |
| 144 | tetrahydropyran-4-yl | methoxyethyl | |
| 145 | tetrahydropyran-4-yl | acetoxymethyl | |
| 146 | tetrahydropyran-4-yl | propionoxyethyl | |
| 147 | 3-diethoxymethyl-tetrahydropyran-4-yl | ethyl | |
| 148 | 3-diethoxymethyl-tetrahydropyran-4-yl | propyl | |
| 149 | 3-methoxymethyl-tetrahydropyran-4-yl | ethyl | |
| 150 | 3-methoxymethyl-tetrahydropyran-4-yl | propyl | |
| 151 | 3-methyl-tetrahydropyran-4-yl | ethyl | |
| 152 | 3-methyl-tetrahydropyran-4-yl | propyl | |
| 153 | $\Delta^2$-dihydropyran-6-yl | ethyl | |
| 154 | $\Delta^2$-dihydropyran-6-yl | propyl | |
| 155 | $\Delta^3$-dihydropyran-3-yl | ethyl | |
| 156 | $\Delta^3$-dihydropyran-3-yl | propyl | |
| 157 | 2,6-dimethyl-$\Delta^3$-dihydropyran-3-yl | ethyl | |
| 158 | 2,6-dimethyl-$\Delta^3$-dihydropyran-3-yl | propyl | |
| 159 | 3,6-dimethyl-$\Delta^2$-dihydropyran-6-yl | ethyl | |
| 160 | 3,6-dimethyl-$\Delta^2$-dihydropyran-6-yl | propyl | |
| 161 | $\Delta^2$-dihydropyran-3-yl | ethyl | |
| 162 | $\Delta^2$-dihydropyran-3-yl | propyl | |
| 163 | tetrahydrothiopyran-3-yl | methyl | |
| 164 | tetrahydrothiopyran-3-yl | ethyl | 1.14(t); 1.6–2.8(m); 3.06(q) |
| 165 | tetrahydrothiopyran-3-yl | propyl | 70–72 |
| 166 | tetrahydrothiopyran-3-yl | isopropyl | |
| 167 | tetrahydrothiopyran-3-yl | butyl | |
| 168 | tetrahydrothiopyran-3-yl | isobutyl | |
| 169 | tetrahydrothiopyran-3-yl | benzyl | |
| 170 | tetrahydrothiopyran-3-yl | phenylethyl | |
| 171 | tetrahydrothiopyran-3-yl | methoxyethyl | 3.55(s); 4.7(s); 17.4(s) |
| 172 | tetrahydrothiopyran-3-yl | acetoxymethyl | |
| 173 | tetrahydrothiopyran-3-yl | propionoxyethyl | |
| 174 | 1-oxo-tetrahydrothiopyran-3-yl | ethyl | |
| 175 | 1-oxo-tetrahydrothiopyran-3-yl | propyl | 0.99(t); 2.97(t); 3.39(m) |
| 176 | 1,1-dioxo-tetrahydrothiopyran-3-yl | ethyl | |
| 177 | 1,1-dioxo-tetrahydrothiopyran-3-yl | propyl | 0.98(t); 1.66(m); 2.98(t) |
| 178 | 2,6-dimethyl-tetrahydrothiopyran-3-yl | ethyl | |
| 179 | 2,6-dimethyl-tetrahydrothiopyran-3-yl | propyl | |
| 180 | 2,6-dimethyl-1-oxo-tetrahydrothiopyran-3-yl | ethyl | |
| 181 | 2,6-dimethyl-1-oxo-tetrahydrothiopyran-3-yl | propyl | |
| 182 | 2,6-dimethyl-1,1-dioxo-tetrahydrothiopyran-3-yl | ethyl | |
| 183 | 2,6-dimethyl-1,1-dioxo-tetrahydrothiopyran-3-yl | propyl | |
| 184 | 4-ethylthio-tetrahydrothiopyran-3-yl | ethyl | |
| 185 | 4-ethylthio-tetrahydrothiopyran-3-yl | propyl | |
| 186 | tetrahydrothiopyran-4-yl | ethyl | |
| 187 | tetrahydrothiopyran-4-yl | propyl | |
| 188 | $\Delta^3$-dihydrothiopyran-3-yl | ethyl | |
| 189 | $\Delta^3$-dihydrothiopyran-3-yl | propyl | 1.01(t); 1.66(m); 5.78(s) |
| 190 | 2,6-dimethyl-$\Delta^3$-dihydrothiopyran-3-yl | ethyl | |
| 191 | 2,6-dimethyl-$\Delta^3$-dihydrothiopyran-3-yl | propyl | |
| 192 | 1-oxo-$\Delta^3$-dihydrothiopyran-3-yl | ethyl | |
| 193 | 1-oxo-$\Delta^3$-dihydrothiopyran-3-yl | propyl | |
| 194 | 1,1-dioxo-$\Delta^3$-dihydrothiopyran-3-yl | ethyl | |
| 195 | 1,1-dioxo-$\Delta^3$-dihydrothiopyran-3-yl | propyl | |
| 196 | $\Delta^3$-dihydrothiopyran-4-yl | ethyl | |
| 197 | $\Delta^3$-dihydrothiopyran-4-yl | cyclopropyl | |
| 198 | $\Delta^3$-dihydrothiopyran-4-yl | propyl | |
| 199 | 5,5-dimethyl-1,3-dioxan-2-yl | ethyl | |
| 200 | 5,5-dimethyl-1,3-dioxan-2-yl | propyl | 67–69 |
| 201 | 2-methyl-1,3-dithian-2-yl | ethyl | |
| 202 | 2-methyl-1,3-dithian-2-yl | propyl | |
| 203 | 1,4-dioxan-2-yl | ethyl | |
| 204 | 1,4-dioxan-2-yl | propyl | 0.95(t); 1.65(m); 3.0(t) |
| 205 | 1,4-dithian-2-yl | ethyl | |

TABLE 1-continued

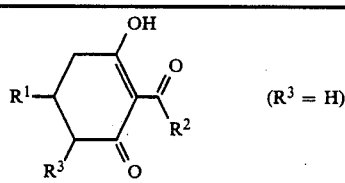

($R^3$ = H)

| Compound no. | $R^1$ | $R^2$ | physical data+ |
|---|---|---|---|
| 206 | 1,4-dithian-2-yl | propyl | 0.99(t); 1.3–1.9(m); 2.1–3.3(m) |
| 207 | 1,3-dithian-5-yl | ethyl | |
| 208 | 1,3-dithian-5-yl | propyl | |
| 209 | 2-pyridyl | ehtyl | |
| 210 | 2-pyridyl | propyl | 0.99(t); 3.50(m); 7.21(m); 7.65(t); 8.56(s) |
| 211 | 2-methyl-pyridin-6-yl | ethyl | 113–15 |
| 212 | 2-methyl-pyridin-6-yl | propyl | 88–92 |
| 213 | 3-pyridyl | ethyl | |
| 214 | 3-pyridyl | propyl | 0.97(t); 7.47(m); 8.56(m) |
| 215 | 2-phenoxy-pyridin-5-yl | ethyl | |
| 216 | 2-phenoxy-pyridin-5-yl | propyl | |
| 217 | 2,6-dichloro-pyridin-3-yl | ethyl | |
| 218 | 2,6-dichloro-pyridin-3-yl | propyl | |
| 219 | 2,4,6-trimethoxypyridin-3-yl | ethyl | |
| 220 | 2,4,6-trimethoxypyridin-3-yl | propyl | |
| 221 | 2,6-dimethoxypyridin-3-yl | ethyl | |
| 222 | 2,6-dimethoxypyridin-3-yl | propyl | |
| 223 | 3-chloro-2,6-dimethoxy-pyridin-5-yl | ethyl | |
| 224 | 3-chloro-2,6-dimethoxy-pyridin-5-yl | propyl | |
| 225 | pyridazin-3-yl | ethyl | |
| 226 | pyridazin-3-yl | propyl | |
| 227 | pyrimidin-5-yl | ethyl | |
| 228 | pyrimidin-5-yl | propyl | |
| 229 | 4,6-dimethoxy-pyrimidin-5-yl | ethyl | |
| 230 | 4,6-dimethoxy-pyrimidin-5-yl | propyl | |
| 231 | 2-methoxypyrimidin-5-yl | ethyl | |
| 232 | 2-methoxypyrimidin-5-yl | propyl | |
| 233 | pyrazin-2-yl | ethyl | |
| 234 | pyrazin-2-yl | propyl | |
| 235 | 1,3-dioxepan-5-yl | ethyl | |
| 236 | 1,3-dioxepan-5-yl | propyl | |
| 237 | 1-(1-isobutoxy-eth-1-yl)-1,3-dioxepan-5-yl | ethyl | |
| 238 | 1-(1-isobutoxy-eth-1-yl)-1,3-dioxepan-5-yl | propyl | |
| 239 | 2-methyl-1,3-dioxepan-5-yl | ethyl | |
| 240 | 2-methyl-1,3-dioxepan-5-yl | propyl | |
| 241 | 2-isopropyl-1,3-dioxepan-5-yl | ethyl | |
| 242 | 2-isopropyl-1,3-dioxepan-5-yl | propyl | |
| 243 | 2-tert-butyl-1,3-dioxepan-5-yl | ethyl | |
| 244 | 2-tert-butyl-1,3-dioxepan-5-yl | propyl | |
| 268 | tetrahydrothiopyran-3-yl | cyclopropyl | 112–113 |
| 269 | tetrahydrothiopyran-3-yl | cyclopropyl | |
| 270 | tetrahydropyran-4-yl | cyclopropyl | |
| 271 | 3-isopropylisoxazol-5-yl | cyclopropyl | |

TABLE 2

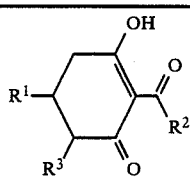

| Compound no. | $R^3$ | $R^2$ | $R^3$ | physical data |
|---|---|---|---|---|
| 245 | tetrahydrothiopyran-3-yl | n-$C_3H_7$ | CN | |
| 246 | tetrahydrothiopyran-3-yl | n-$C_3H_7$ | $COOCH_3$ | |
| 247 | tetrahydropyran-3-yl | n-$C_3H_7$ | $COOCH_3$ | |
| 248 | tetrahydropyran-4-yl | $CH_3$ | $COOCH_3$ | |
| 249 | tetrahydropyran-4-yl | $C_2H_5$ | $COOCH_3$ | |
| 250 | tetrahydropyran-4-yl | n-$C_3H_7$ | $COOCH_3$ | |
| 251 | tetrahydropyran-4-yl | n-$C_4H_9$ | $COOCH_3$ | |
| 252 | tetrahydropyran-4-yl | $C_2H_5$ | CN | |
| 253 | 6-methoxy-tetrahydropyran-2-yl | n-$C_3H_7$ | $COOCH_3$ | |
| 254 | 4-methyl-tetrahydropyran-3-yl | n-$C_3H_7$ | $COOCH_3$ | |

TABLE 2-continued

Structure: cyclohexenone with OH, R¹, R², R³ substituents and C=O group

| Compound no. | R³ | R² | R³ | physical data |
|---|---|---|---|---|
| 255 | 3-pyridyl | n-C₃H₇ | COOCH₃ | |
| 256 | 2-isopropyl-1,3-dioxepan-5-yl | C₂H₅ | COOCH₃ | |
| 257 | 2-isopropyl-1,3-dioxepan-5-yl | n-C₃H₇ | COOCH₃ | |
| 258 | 2-methyl-tetrahydrofuran-3-yl | n-C₃H₇ | COOCH₃ | 0.97(t); 1.22(d); 3.84(s) |

TABLE 3

Salts of the formula II $$\text{(II)}$$

where R¹ = tetrahydrothiopyran-3-yl,
R² = n-propyl and
R³ = H

| Compound no. | M |
|---|---|
| 259 | sodium |
| 260 | potassium |
| 261 | barium |
| 262 | copper (II) |
| 263 | triethylammonium |
| 264 | tri-n-butylammonium |
| 265 | benzyltrimethylammonium |
| 266 | trimethylsulfonium |
| 267 | trimethylsulfoxonium |

The cyclohexanone derivatives of the formula I may have a variety of influences on practically all plant development stages, and are therefore used as growth regulators.

The active ingredients to be used in accordance with the invention may be applied to the crop either by treating the seed, treating the soil (i.e., via the roots), or—the method particularly preferred—by spraying the leaves.

Because the active ingredients are well tolerated by the crop plants, application rates may vary within a wide range.

When the active ingredients are used to treat seed, active ingredient amounts of from 0.001 to 50 g, preferably from 0.01 to 10 g, per kg of seed are generally required.

When the active ingredients are applied to the soil or foliage, amounts of from 0.01 to 12 kg/ha, preferably from 0.25 to 3 kg/ha, are generally considered to be sufficient.

The formulations and the ready-to-use application forms prepared therefrom, e.g. solutions, emulsions, suspensions, powders, dusts, pastes or granules, are applied in known manner, for example preemergence, postemergence or as seed dressings.

Examples of formulations are given below.

I. 20 parts by weight of the compound of Example 64 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

II. 3 parts by weight of the compound of Example 64 is intimately mixed with 97 parts by weight of particulate kaolin. A dust is obtained containing 3% by weight of the active ingredient.

III. 30 parts by weight of the compound of Example 115 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

IV. 40 parts by weight of the compound of Example 137 is intimately mixed with 10 parts of the sodium salt of a phenolsulonic acid-urea-formaldehyde condensate, 2 parts of silica gel and 48 parts of water to give a stable aqueous dispersion. Dilution in 100,000 parts by weight of water gives an aqueous dispersion containing 0.04 wt % of active ingredient.

V. 20 parts of the compound of Example 164 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

VI. 90 parts by weight of the compound of Example 214 is mixed with 10 parts by weight of N-methyl-alpha-pyrrolidone. A mixture is obtained which is suitable for application in the form of very fine drops.

VII. 20 parts by weight of the compound of Example 138 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

VIII. 20 parts by weight of the compound of Example 165 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IX. 20 parts by weight of the compound of Example 137 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

The agents according to the invention may, in these application forms, also be mixed and applied with other active ingredients, e.g., herbicides, insecticides, other growth regulators, fungicides and fertilizers. When mixed with other growth regulators, synergistic effects also occur; i.e., the action of the combination product is greater than the effect of the individual components added together.

To determine the growth-regulating properties of the compounds, a culture substrate provided with sufficient nutrients was filled into plastic pots 12.5 cm in diameter, and test plants were grown therein.

The experiments show that for instance compounds nos. 64, 115, 137, 164 and 214, applied postemergence as aqueous formulations, have significant growth-regulating properties.

In 2 special series experiments, in which the comparative agent was the commerical product chlormequat chloride, compounds nos. 40, 50, 52, 54 and 124 has a special effect on stem length or internodal distance in spring barley at application rates of as low as 1.5 to 6 mg per vessel. Compounds nos. 50, 52 and 54 also had a special influence on steam length or internodal distance in rice at application rates of as low as 1.5 to 6 mg per vessel.

Compounds nos. 64, 137, 138, 164 and 165 selected by way of example and which were employed together with a nutrient solution, also exhibited significant growth-regulating properties.

We claim:

1. A composition for regulating plant growth, containing an effective amount of at least one cyclohexenone derivative of the formula

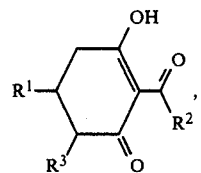

where $R^1$ is a thiazole group which may contain up to 3 substituents from the group consisting of alkyl, alkenyl, alkoxy, alkoxyalkyl or alkylthio, each of 1 to 6 carbon atoms, cyclohexyl, cyclohexoxy, phenyl which is unsubstituted or substituted by methyl, chloro or methoxy, phenoxy which is unsubstituted or substittued by methyl, chloro or methoxy, halogen, nitro or dialkylamino, $R^2$ is alkyl of 1 to 4 carbon atoms, alkoxyalkyl of 1 to 4 carbon atoms, cyclopropyl, benzyl, phenylethyl or acyloxyalkyl of up to 6 carbon atoms, and $R^3$ is hydrogen, alkoxycarbonyl of 2 to 5 carbon atoms or cyano, or a salt thereof, and a liquid or solid carrier.

2. A process for regulating plant growth, wherein a growth regulating amount at least one cyclohexenone derivative of the formula I as set forth in claim 1 is allowed to act on plants or their biotope.

3. A composition as defined in claim 1, wherein $R^1$ is cyclohexenone derivative of the formula I is 2-dimethylamino-thiazol-5-yl, $R^2$ is propyl and $R^3$ is hydrogen.

4. A process for regulating plant growth, wherein a growth regulating amount of the composition of claim 3 is allowed to act on the plants or their biotope.

5. A cyclohexenone derivative of the formula

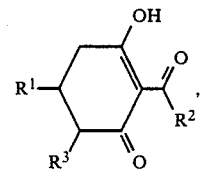

where $R^1$ is a thiazole group which may contain up to 3 substituents from the group consisting of alkyl, alkenyl, alkoxy, alkoxyalkyl or alkylthio, each of 1 to 6 carbon atoms, cyclohexyl, cyclohexoxy, phenyl which is, unsubstituted or substituted by methyl, chloro or methoxy, phenoxy which is unsubstituted or substituted by methyl, chloro or methoxy, halogen, nitro or dialkylamino, $R^2$ is alkyl of 1 to 4 carbon atoms, alkoxyalkyl of 1 to 4 carbon atoms, cyclopropyl, benzyl, phenylethyl or acyloxyalkyl of up to 6 carbon atoms, and $R^3$ is hydrgoen, alkoxycarbonyl of 2 to 5 carbon atoms or cyano, or a salt thereof.

6. A cyclohexenone derivative as defined in claim 5, wherein $R^1$ of the cyclohexenone derivative of the formula I is 2-dimethylamino-thiazol-5-yl, $R^2$ is propyl and $R^3$ is hydrogen.

* * * * *

UNITED STATES PATENT AND TRADEMARK OFFICE
CERTIFICATE OF CORRECTION

PATENT NO. : 4,948,415

DATED : August 14, 1990

INVENTOR(S) : Michael KEIL et al.

It is certified that error appears in the above-identified patent and that said Letters Patent is hereby corrected as shown below:

Column 14, line 14, (Claim 1, line 10) "substittued" should read --substituted--

Column 14, line 22, (Claim 2, line 2) after "amount" insert --of--

Column 14, line 44, (Claim 5, line 6) after "which" delete ","

Column 14, lines 50-51, (Claim 5, line 12) "hydrgoen" should read --hydrogen--

Signed and Sealed this

Twentieth Day of August, 1991

*Attest:*

HARRY F. MANBECK, JR.

*Attesting Officer*   *Commissioner of Patents and Trademarks*